United States Patent [19]

Behre et al.

[11] Patent Number: 4,873,026
[45] Date of Patent: Oct. 10, 1989

[54] PROCESS FOR THE PREPARATION OF 1-AMINONAPHTHALENE-2,4,7-TRISULPHONIC ACID AND 1-AMINONAPHTHALENE-7-SULPHONIC ACID

[75] Inventors: Horst Behre; Heinz U. Blank, both of Odenthal; Gerhard Marzolph; Willi Streicher, both of Koeln, all of Fed. Rep. of Germany

[73] Assignee: Bayer Aktiengesellschaft, Leverkusen, Fed. Rep. of Germany

[21] Appl. No.: 253,280

[22] Filed: Oct. 4, 1988

Related U.S. Application Data

[63] Continuation of Ser. No. 900,215, Aug. 26, 1986, abandoned.

[30] Foreign Application Priority Data

Sep. 7, 1985 [DE] Fed. Rep. of Germany ....... 3531923

[51] Int. Cl.$^4$ .......................................... C07C 143/60
[52] U.S. Cl. .......................................... 562/72
[58] Field of Search .......................................... 260/508

[56] References Cited

FOREIGN PATENT DOCUMENTS 22545 9/1882 Fed. Rep. of Germany .
15223 6/1894 United Kingdom .

OTHER PUBLICATIONS

Donaldson, "The Chemistry and Technology of Naphthalene Compounds", Edward Arnold (Publishers) Ltd., 1958, pp. 184–191, 198–199 and 208–209.

*Primary Examiner*—Nicky Chan
*Attorney, Agent, or Firm*—Sprung, Horn, Kramer & Woods

[57] ABSTRACT

New process for the preparation of 1-aminonaphthalene-2,4,7-trisulphonic acid and, if appropriate, 1,7-Cleve's acid, in which 1-nitronaphthalene is reacted by the Piria method with bisulphites in a manner which is known per se, the sulphamate mixture obtained in this Piria reaction is sulphonated with sulphur trioxide in sulphuric acid to give 1-aminonaphthalene-2,4,7-trisulphonic acid and, if appropriate, this is hydrolysed to 1,7-Cleve's acid by heating in aqueous sulphuric acid.

7 Claims, No Drawings

PROCESS FOR THE PREPARATION OF 1-AMINONAPHTHALENE-2,4,7-TRISULPHONIC ACID AND 1-AMINONAPHTHALENE-7-SULPHONIC ACID

This is a continuation of application Ser. No. 900,215, filed Aug. 26, 1986 now abandoned.

The invention relates to a new process for the preparation of 1-aminonaphthalene-2,4,7-trisulphonic acid and 1-aminonaphthalene-7-sulphonic acid (1,7-Cleve's acid) from 1-nitronaphthalene.

1,7-Cleve's acid is an important intermediate product for the preparation of dyestuffs (see Ullmanns Enzyklopädie der Technischen Chemie (Ullmann's Encyclopaedia of Industrial Chemistry), 4th edition, 1979, Volume XVII, pages 109–110).

1,7-Cleve's acid has hitherto been prepared in a multistage process from naphthalene via naphthalene-$\beta$-sulphonic acid, which is nitrated to give a mixture of 5-nitro- and 8-nitronaphthalene-2-sulphonic acid. The mixture of the two isomeric nitronaphthalenesulphonic acids is resolved into the two isomers and the isomers are reduced to 1,7-Cleve's acid and 1,6-Cleve's acid. The two Cleve's acids are each obtained in a yield of 34% of theory (see Winnacker-Küchler, Chemische Technologie (Chemical Technology), 2nd edition, 1959, Volume 3: Organische Technologie I (Organic Technology I), pages 868–869). However, the resolution into the individual isomers can also first take place at the stage of the aminonaphthalenesulphonic acids (see Winnacker-Küchler, Chemische Technologie (Chemical Technology), 4th edition, 1982, Volume 6; Organische Technologie II (Organic Technology II), page 264). The disadvantages of these two processes are the low yield of 1,7-Cleve's acid and the 1,6-Cleve's acid unavoidably obtained.

There has therefore been no lack of attempts to discover processes which give better yields of 1,7-Cleve's acid without 1,6-Cleve's acid being unavoidably obtained. Thus, the preparation of 1,7-Cleve's acid by ammonolysis and desulphonation of 1-chloronaphthalene-4,7-disulphonic acid is described in DE-OS (German Published Specification) 2,535,377. This process has the disadvantage, however, that pure 1-chloronaphthalene is required for the preparation of the 1-chloronaphthalene-4,7-disulphonic acid and this is not inexpensively available industrially.

The preparation of 1,7-Cleve's acid by sulphonation of 1-naphthol with subsequent hydrolysis to 1-naphthol-7-sulphonic acid and a subsequent Bucherer reaction is described in Yuki Gosei Kagaku Kyokai Shi 29 (1971) 12, 1129 (Chemical Abstract 76, 140 292 R). However, this process has the disadvantages that it requires intermediate isolation of the 1-naphthol-7-sulphonic acid and leads to good yields only if aqueous hydrochloric acid is used for the hydrolysis. The process is consequently expensive and presents considerable corrosion problems.

It is furthermore known from Donaldson, The Chemistry and Technology of Naphthalene Compounds, 1959, pages 198 and 209 that 1,7-Cleve's acid is formed in the hydrolysis of 1-naphthylamine-2,7-disulphonic acid with 80% strength sulphuric acid or in the hydrolysis of 1-naphthylamine-2,4,7-trisulphonic acid in boiling 75% strength sulphuric acid. These two procedures are, however, of no interest industrially because as yet no economic preparation processes are known for the starting compounds, the 1-aminonaphthalene-2,4,7-trisulphonic acid and the 1-aminonaphthalene-2,7-disulphonic acid. The following processes have so far been proposed for the preparation of 1-naphthylamine-2,4,7-trisulphonic acid:

1. The reaction of 1-aminonaphthalene-4-sulphonic acid (naphthionic acid) with 3 to 4 parts of 40% strength oleum at 120° C. (see Friedländer I, page 331: German Patent Specification 22,545). However, it is already pointed out in the description of the patented process that the trisulphonic acid is obtained in only an unsatisfactory yield because naphthionic acid is oxidatively degraded by oleum under the influence of heat. In British Patent Specification No. 15,223 (1893), it is furthermore pointed out in the discussion of the process described in German Patent Specification No. 22,545 that at least two isomeric trisulphonic acids, namely 1-aminonaphthalene-2,4,6- and 1-aminonaphthalene-2,4,7-trisulphonic acid, are formed in the reaction of naphthionic acid with oleum.

2. The reaction of 1-aminonaphthalene-7-sulphonic acid (1,7-Cleve's acid) or 1-aminonaphthalene-4,7-disulphonic acid or salts thereof with oleum at temperatures of 50° to 100° C. (British Patent Specification No. 15,223 (1893). This process is of no interest industrially, because it requires 1,7-Cleve's acid or 1-aminonaphthalene-4,7-disulphonic acid as starting compounds and these in turn are also accessible only with difficulty and via many preparation and purification stages (for removal of the isomers). The process described in Friedlander I, page 407 (=German Patent Specification 41,957) for the preparation of 1-naphthylamine-4,7-disulphonic acid by sulphonation of naphthionic acid is unsuitable for a procedure on an industrial scale, because 1-naphthylamine-4,7-disulphonic acid is obtained as a mixture with the isomeric 1-naphthylamine-4,6-disulphonic acid. Separation of the disulphonic acid mixture obtained via the calcium salt would indeed be possible, but is of no interest industrially. Furthermore, no yields are quoted for the process.

Surprisingly, it has now been found that 1-aminonaphthalene-2,4,7-trisulphonic acid can be obtained in good yields and virtually free from isomers from starting compounds which are easily accessible industrially if 1-nitronaphthalene is subjected to reducing sulphonation by the action of bisulphites (that is to say in accordance with the Piria method) and the sulphamate mixture which is obtained in this Piria reaction and essentially consists of the ammonium and/or alkali metal sulphamates of 1-aminonaphthalene, of 1-naphthylamine-4-sulphonic acid (naphthionic acid) and of 1-naphthylamine-2,4-disulphonic acid and which, if appropriate, also contains ammonium and/or alkali metal bisulphates formed during the reaction, is sulphonated with sulphur trioxide in sulphuric acid.

The reaction of 1-nitronaphthalene by the Piria method with bisulphites is known per se (see, for example, R. Piria, Ann. 78 (1851), 31–68: J. Am. Chem. Soc. 53 (1931), 1432–1442 and 1443–1447: J. Am. Chem. Soc. 58 (1936), 225–228: J. Org. Chem. 13 (1948), 179). Since the Piria reaction of 1-nitronaphthalene leads not to a single compound but to mixtures of the sulphamates of 1-naphthylamine, of 1-naphthylamine-4-sulphonic acid (naphthionic acid) and of 1-naphthylamine-2,4-disulphonic acid or, after hydrolysis of the sulphamates, to mixtures of the corresponding free amines, from which the individual amines can be isolated only with the aid of expensive separation processes, the Piria reaction of 1-nitronaphthalene has hitherto achieved no industrial importance at all.

According to the invention, it has been found that this sulphamate mixture obtained in the Piria reaction of 1-nitronaphthalene is an extremely advantageous starting material for the preparation of 1-aminonaphthalene-2,4,7-trisulphonic acid. The sulphamate mixture as such can be prepared easily from inexpensive starting compounds which are readily accessible industrially, and when sulphonated with sulphur trioxide, 1-aminonaphthalene-2,4,7-trisulphonic acid is obtained in good yields and virtually free from isomers.

Surprisingly, no oxidative degradation takes place during the sulphonation of the sulphamate mixture and the sulphonation selectively attacks the still free 2-, 4- and 7-positions of the sulphamates or of the amines formed from them during the reaction. According to the invention, it has been found that the ammonium and/or alkali metal (bi)sulphates contained in the sulphamate mixture, and above all the ammonium and/or alkali metal (bi)sulphates formed during the sulphonation of the sulphamate mixture, effect selective sulphonation of the 2-, 4- and 7-positions in the sulphamates and prevent oxidative degradation.

The invention therefore relates to a new process for the preparation of 1-aminonaphthalene-2,4,7-trisulphonic acid, which is characterized in that 1-nitronaphthalene is reacted by the Piria method with bisulphites in a manner which is known per se, the sulphamate mixture obtained in this Piria reaction is sulphonated with sulphur trioxide in sulphuric acid and the resulting 1-aminonaphthalene-2,4,7-trisulphonic acid is isolated from the sulphonation mixture in a manner which is known per se.

This new process for the preparation of 1-aminonaphthalene-2,4,7-trisulphonic acid at the same time opens up a new economic process for the preparation of 1,7-Cleve's acid, since 1,7-Cleve's acid is obtainable in good yields from 1-aminonaphthalene-2,4,7-trisulphonic acid by hydrolysis.

The invention thus also relates to a new process for the preparation of 1,7-Cleve's acid, which is characterized in that 1-nitronaphthalene is reacted by the Piria method with bisulphites in a manner which is known per se, the sulphamate mixture obtained in this Piria reaction is sulphonated with sulphur trioxide and the sulphonation mixture or the 1-aminonaphthalene-2,4,7-trisulphonic acid isolated from it is hydrolysed by warming in aqueous sulphuric acid.

The sulphonation according to the invention of the sulphamate mixture obtained in the Piria reaction of 1-nitronaphthalene is carried out at temperatures of 10°–150° C., preferably 30°–120° C.

The sulphur trioxide used for the sulphonation is employed in the form of oleum, preferably oleum containing 20 to 100% by weight, particularly preferably 40 to 70% by weight of sulphur trioxide. The oleum is used in an amount such that 1.5 to 10 mol, preferably 2 to 6 mol, of sulphur trioxide are present per mol of 1-nitronaphthalene employed in the Piria reaction.

The sulphamate mixtures to be used as the starting material for the sulphonation according to the invention are obtainable in a manner which is known per se, for example by heating 1-nitronaphthalene with aqueous ammonium bisulphite solution, if appropriate with the addition of ammonia, or with aqueous alkali metal bisulphite solution, if appropriate with the addition of an alkali, at the reflux temperature until a clear solution has formed. This aqueous solution of the ammonium and/or alkali metal sulphamate, which essentially consists of a mixture of the sulphamates of 1-naphthylamine, of naphthionic acid and of 1-naphthylamine-2,4-disulphonic acid and the ammonium and/or alkali metal bisulphates formed during the reaction, is freed from water, for example by concentration on a rotary evaporator and subsequent drying of the residue in vacuo at elevated temperature down to a residual water content of 0 to 10% by weight.

A particularly advantageous starting material for the sulphonation according to the invention is obtained, for example, when 1 mol of 1-nitronaphthalene, suspended in 1 to 2 l of water, is heated with 3 to 5 mol of ammonium bisulphite, preferably in the form of a 40 to 50% strength by weight aqueous solution, and 1.5 to 3 mol of ammonia, preferably in the form of an approximately 25% strength by weight aqueous solution, at 100° to 105° C. until a clear solution has formed. During the reaction, the pH value of the solution falls from 6 to 6.5 to 5 to 5.5. After evaporation of the reaction solution in a rotary evaporator and drying of the residue in vacuo, a product of the following composition is obtained: 9.1% by weight of 1-NH-SO$_3$NH$_4$-C$_{10}$H$_6$-4-SO$_3$NH$_4$, 49.3% by weight of 1-NH-SO$_3$NH$_4$-C$_{10}$H$_5$-2,4-(SO$_3$NH$_4$)$_2$, 3.0% by weight of 1-NH-SO$_3$NH$_4$-C$_{10}$H$_6$-2-SO$_3$NH$_4$, 0.7% by weight of 1-NH-SO$_3$NH$_4$-C$_{10}$H$_5$-4,7-(SO$_3$NH$_4$)$_2$, 1.8% by weight of water, 36.1% by weight of ammonium bisulphate+, if appropriate, small amounts of ammonium bisulphite and organic by-products of unknown structure.

The composition of the sulphamate mixture was determined by means of high pressure liquid chromatography (HPLC) after cleavage of the sulphamates with mineral acid.

If the sulphamate mixtures to be employed as the starting material for the sulphonation according to the invention still contain water, it is advisable for sulphur trioxide (oleum) also additionally to be added for the sulphonation, as well as the amount of sulphur trioxide (oleum) required for the sulphonation, in order to bind the water.

The sulphonation according to the invention of the sulphamate mixture can be carried out in various ways:

For example, it is possible first to suspend the sulphamate mixture in anhydrous sulphuric acid, to add the envisaged amount of oleum slowly to the suspension, to increase the temperature of the reaction mixture continuously or stepwise from 10° C. to 150° C., preferably from 30° C. to 120° C., during the addition of the oleum and to bring the sulphonation to completion at 80° to 150° C., preferably 90° to 120° C.

In order to improve the stirrability of the reaction mixtures, however, it has proved more advantageous to take anhydrous H$_2$SO$_4$, to meter the dried sulphamate mixture and the required amount of oleum simultaneously into this initial material at temperatures of 10° to 150° C., preferably 30° to 120° C., and to bring the reaction to completion at 80° to 150° C., preferably 90° to 120° C.

The sulphonation mixture present after conclusion of the sulphonation is a solution or suspension of 1-aminonaphthalene-2,4,7-trisulphonic acid in sulphuric acid; it contains only small amounts of isomeric 1-aminonaphthalene-2,4,6-trisulphonic acid. The 1-aminonaphthalene-2,4,7-trisulphonic acid can be isolated from the sulphonation mixture by dilution with water. However, it is also possible to use the sulphonation mixture directly for the preparation of the 1,7-Cleve's acid.

The hydrolysis of the 1-aminonaphthalene-2,4,7-trisulphonic acid to give 1,7-Cleve's acid is carried out in 60 to 80% strength, preferably 60 to 75% strength, aqueous sulphuric acid at temperatures of 140° to 170° C., preferably 145° to 165° C. The hydrolysis takes about 0.5 to 10 hours.

The 1,7-Cleve's acid can be precipitated from the hydrolysis mixture by dilution to 30 to 60% strength sulphuric acid (percent by weight). The acid precipitated is filtered off with suction, washed with water and dried. It is free from 1,6-Cleve's acid.

The 1,7-Cleve's acid is obtained as the free acid; if desired, it can be converted into the desired salts in a known manner, for example by neutralization of its aqueous suspension with corresponding bases.

For the—preferred—case where the sulphonation mixture obtained during sulphonation of the sulphamate mixture is hydrolysed directly, the sulphonation mixture is simply mixed with water in an amount such that 60 to 80% strength sulphuric acid is formed. The sulphonation mixture is advantageously mixed with the water by a procedure in which the sulphonation mixture is introduced into the water, the temperature thereby being kept as close as possible to the boiling point of the hydrolysis mixture. The mixture is then stirred at 140° to 170° C. for several hours and, when the hydrolysis has ended, further water is added to precipitate the 1,7-Cleve's acid.

For isolation of the 1,7-Cleve's acid, it may also be advantageous, when the hydrolysis has ended, for the sulphuric acid to be removed as gypsum by addition of calcium carbonate and/or calcium oxide/hydroxide and, after filtering off the gypsum, for the 1,7-Cleve's acid to be precipitated out of the filtrate in a very easily filterable form by acidification with a mineral acid, preferably hydrochloric acid.

EXAMPLE 1

(a) Preparation of the Sulphamate Mixture

A mixture of 86.5 g (0.5 mol) of 1-nitronaphthalene, 70 g (1.0 mol) of 25% strength by weight $NH_3$ solution, 427 g (2.0 mol) of 46.4% strength by weight aqueous $NH_4HSO_3$ solution and 700 g of water is heated at the reflux temperature (about 101° C.) in a 2 l four-necked flask equipped with a stirrer, reflux condenser, glass electrode and internal thermometer until the 1-nitronaphthalene has dissolved completely (heating time: about 5 hours). During the heating, the pH value of the reaction mixture falls from 6.3 to 5.2.

The reaction solution is then concentrated to dryness in a rotary evaporator and dried to constant weight in vacuo at 100° C. 276 g of a product of the following composition are obtained: 9.1% by weight of 1-NH-$SO_3NH_4$-$C_{10}H_6$-4-$SO_3NH_4$, molecular weight 337, 49.3% by weight of 1-NH-$SO_3NH_4$-$C_{10}H_5$-2,4-$(SO_3NH_4)_2$, molecular weight 434, 3.0% by weight of 1-NH-$SO_3NH_4$-$C_{10}H_6$-2-$SO_3NH_4$, molecular weight 337, 0.7% by weight of 1-NH-$SO_3NH_4$-$C_{10}H_5$-4,7-$(SO_3NH_4)_2$, molecular weight 434, 1.8% by weight of water and 36.1% by weight of ammonium bisulfate+if appropriate, small amounts of ammonium bisulphite and organic byproducts of unknown structure.

The composition of the product was determined by HPLC after acid hydrolysis of the sulphamates by means of a mineral acid.

(b) Sulphonation of the Sulphamate Mixture 196 g (2.0 mol) of 100% strength by weight $H_2SO_4$ are taken in a sulphonating flask equipped with a stirrer, internal thermometer, condenser, metering dropping funnel and metering device for solids and are warmed to 95° to 100° C. After flushing the apparatus with dry nitrogen, 200 g of 65% strength oleum (1.6 mol of $SO_3$, 0.22 mol of this for binding the water contained in the sulphamate mixture) are added dropwise and at the same time 221 g of sulphamate mixture ($\triangleq$ 0.4 mol of 1-nitronaphthalene) are metered in, at 95° to 100° C. in the course of 2 hours.

The reaction mixture is subsequently stirred at 95° to 100° C. for 3 hours. The following composition of the sulphonation mixture was determined by means of HPLC: 17.8% by weight of 1-naphthylamine-2,4,7-trisulphonic acid, molecular weight 383, 0.2% by weight of 1-naphthylamine-2,4,6-trisulphonic acid, molecular weight 383, 1.2% by weight of 1-naphthylamine-2,4-disulphonic acid, molecular weight 303, 0.2% by weight of 1-naphthylamine-4,6-disulphonic acid, molecular weight 303 and 0.1% by weight of 1-naphthylamine-4,7-disulphonic acid, molecular weight 303.

The yield of 1-naphthylamine-2,4,7-trisulphonic acid is thus 72% of theory, based on the 1-nitronaphthalene employed.

(c) Acid Hydrolysis of the Sulphonation Mixture and Isolation of the 1,7-Cleve's Acid 170 g of water are allowed to run into the sulphonation mixture at 100° C. in the course of about 1 hour; the temperature thereby rises to about 130° C. The reaction mixture is warmed up to its boiling point (about 155° C.) and kept at this temperature for about 2 hours.

Analysis of the hydrolysis mixture by means of HPLC gave the following composition: 6.60% by weight of 1-naphthylamine-7-sulphonic acid, molecular weight 223, 0.07% by weight of 1-naphthylamine-6-sulphonic acid, molecular weight 223, 0.23% by weight of 1-naphthylamine-4,7-disulphonic acid, molecular weight 303, 0.21% by weight of 1-naphthylamine-4,6-disulphonic acid, molecular weight 303 and 0.23% by weight of 1-naphthylamine-2,7-disulphonic acid, molecular weight 303.

The yield of 1-naphthylamine-7-sulphonic acid is thus about 58% of theory, based on the 1-nitro-naphthalene employed.

To isolate the 1,7-Cleve's acid, the reaction mixture is diluted with about 400 g of water, the sulphuric acid is converted into $CaSO_4$ by addition of about 850 g of a 60% strength by weight aqueous $CaCO_3$ suspension and the gypsum is filtered off and washed with water. The combined filtrates are acidified down to a pH value of about 1 with about 190 g of 30% strength by weight HCl at 80° C. The suspension obtained in this manner is cooled to about 20° C. in the course of several hours; the 1,7-Cleve's acid precipitated is filtered of and washed with cold water. 58 g of 1,7-Cleve's acid (moist) are obtained with the following composition, determined by HPLC: 78.1% by weight of 1-naphthylamine-7-sulphonic acid, molecular weight 223, 0.3% by weight of 1-naphthylamine-6-sulphonic acid, molecular weight 223 and 0.5% by weight of 1-naphthylamine-4,7-disulphonic acid, molecular weight 303.

The yield of 1,7-Cleve's acid isolated is thus about 51% of theory, based on the 1-nitronaphthalene employed.

EXAMPLE 2

(a) 583 g of sulphamate mixture (dried product) are obtained from 173 g (1.0 mol) of 1-nitronaphthalene, 140 g (2.0 mol) of 25% strength by weight aqueous $NH_3$ solution, 778 g (4.0 mol) of 51% strength by weight aqueous $NH_4HSO_3$ solution and 1,500 g of $H_2O$ under the conditions described in Example 1(a).

(b) 235 g (2.4 mol) of 100% strength by weight $H_2SO_4$ are taken in the sulphonating apparatus described in Example 1. 222 g of 65% strength oleum (1.8 mol of $SO_3$) are added dropwise and at the same time 233 g ($\triangleq$ 0.4 mol of 1-nitronaphthalene) of sulphamate mixture are metered in, at 10° to 15° C. The reaction mixture is warmed to 95° C. and stirred at 95° C. for 2 hours, 160 g of $H_2O$ are slowly added, whereupon the temperature rises to 155° C., the mixture is stirred at 155° C. for 90 minutes, 400 g of $H_2O$ are added and the mixture is cooled to 50° C. The 1,7-Cleve's acid precipitated is filtered off and washed several times with cold water. 86 g of 1,7-Cleve's acid (moist) are obtained with the following composition, determined by means of HPLC: 51.0% by weight of 1-naphthylamine-7-sulphonic acid, molecular weight 223, 0.05% by weight of 1-naphthylamine-4,7-disulphonic acid, molecular weight 303 and 1.2% by weight of 1-naphthylamine-2,7-disulphonic acid, molecular weight 303.

The yield of 1,7-Cleve's acid isolated is thus 49% of theory, based on the 1-nitronaphthalene employed.

EXAMPLE 3.

(a) 86.5 g (0.5 mol) of 1-nitronaphthalene, 20 g (0.5 mol) of NaOH, 190 g of $Na_2S_2O_5$ (1.0 mol $\triangleq$ 2.0 mol of $NaHSO_3$) and 1,000 g of $H_2O$ are heated at the reflux temperature in the apparatus described in Example 1(a) until a clear solution has formed. After drying, 293 g of a sulphamate mixture of the following composition are obtained (determined by HPLC after acid hydrolysis with mineral acids): 8.1% by weight of 1-NH-SO$_3$Na-C$_{10}$H$_6$-4-SO$_3$Na, molecular weight 347, 47.9% by weight of 1-NH-SO$_3$Na-C$_{10}$H$_5$-2,4-(SO$_3$Na)$_2$, molecular weight 449, 3.4% by weight of 1-NH-SO$_3$Na-C$_{10}$H$_7$, molecular weight 245, 2.0% by weight of $H_2O$ and 38.6% by weight of $NaHSO_4$+organic byproducts of unknown structure.

(b) 196 g (2.0 mol) of 100% strength by weight $H_2SO_4$ are taken in the sulphonation apparatus described in Example 1(b). 65% strength by weight oleum (2.1 mol of $SO_3$, 0.26 mol of this for binding the water in the sulphamate mixture) are added dropwise and at the same time 234.5 g ($\triangleq$ 0.4 mol of 1-nitronaphthalene) of sulphamate mixture are metered in, at 30° to 40° C. in the course of 2 hours.

The reaction mixture is subsequently stirred at 90° C. for 4 hours. Analysis of the sulphonation mixture by means of HPLC gave the following composition: 16.9% by weight of 1-naphthylamine-2,4,7-trisulphonic acid, molecular weight 383, 0.5% by weight of 1-naphthylamine-2,4,6-trisulphonic acid, molecular weight 383, 0.22% by weight of 1-naphthylamine-2,4-disulphonic acid, molecular weight 303, 0.14% by weight of 1-naphthylamine-4,7-disulphonic acid, molecular weight 303 and 0.07% by weight of 1-naphthylamine-4,6-disulphonic acid, molecular weight 303.

The yield of 1-naphthylamine-2,4,7-trisulphonic acid is thus 76% of theory, based on the 1-nitronaphthalene employed.

(c) The sulphonation mixture is introduced into 205 g of $H_2O$ at 80° C. in the course of about 1 hour, whereupon the temperature rises to 155° C. The reaction mixture is kept at 155° C. for 5 hours, diluted with 245 g of $H_2O$, cooled to 50° C. and stirred at 50° C. for about 30 minutes. The 1,7-Cleve's acid precipitated is filtered off, washed several times with cold water until free from acid and dried in vacuo at 80° C. 43.5 g of 1,7-Cleve's acid (dry) of the following composition are obtained: 96.1% by weight of 1-naphthylamine-7-sulphonic acid, molecular weight 223, <0.05% by weight of 1-naphthylamine-6-sulphonic acid, molecular weight 223, 1.0% by weight of 1-naphthylamine-2-sulphonic acid, molecular weight 223, 0.1% by weight of 1-naphthylamine-4,7-disulphonic acid, molecular weight 303, <0.05% by weight of 1-naphthylamine-2,4-disulphonic acid, molecular weight 303, <0.05% by weight of 1-naphthylamine-2,7-disulphonic acid, molecular weight 303 and <0.05% by weight of 1-naphthylamine-4,6-disulphonic acid, molecular weight 303.

The yield of 1,7-Cleve's acid isolated is thus 47% of theory, based on the 1-nitronaphthalene employed.

What is claimed is:

1. A process for the preparation of 1-aminonaphthalene-2,4,7-trisulphonic acid which comprises the steps
    (a) reacting 1-nitronaphthalene by the Piria method with bisulphites,
    (b) sulphonating the sulphamate mixture obtained in this Piria reaction with sulphur trioxide in sulphuric acid and
    (c) isolating the 1-amino-naphthalene-2,4,7-trisulphonic acid from the sulphonation mixture.

2. The process of claim 1, wherein the sulphur trioxide is employed in the form of oleum.

3. The process of claim 2, wherein the sulphur trioxide is employed in the form of 20 to 100% strength by weight oleum.

4. The process according to claim 1, wherein the amount of sulphur trioxide is chosen so that 1.5 to 10 mol of sulphur trioxide are present per mol of 1-nitronaphthalene employed in the Piria reaction.

5. The process according to claim 1, wherein the sulphamate mixtures employed are those mixtures which are obtained on concentration of those aqueous reaction solutions obtained when 1 mol of 1-nitronaphthalene, suspended in water, is heated with an aqueous solution of 3 to 5 mol of ammonium or alkali metal bisulphite and 1.5 to 3 mol of ammonia or aqueous alkali metal hydroxide solution to 100° to 105° C.

6. A process for the preparation of 1-aminonaphthalene-7-sulphonic acid (1,7-Cleve's acid) from 1-nitronaphthalene, which process comprises
    (a) reacting 1-nitronaphthalene by the Piria method with bisulphites,
    (b) sulphonating the sulphamate mixture obtained in this Piria reaction with sulphur trioxide in sulphuric acid and
    (c) hydrolysing the sulphonation mixture obtained in step (b).

7. The process of claim 6, wherein the hydrolysis is carried out in 60 to 80% strength sulphuric acid.

* * * * *